US 6,589,540 B1

Jul. 8, 2003

(54) COSMETIC COMPOSITION FOR SKIN CARE CONTAINING RETINOL AND EPIDERMAL GROWTH FACTOR

(75) Inventor: Byoung Kee Jo, Anyang-si (KR)

(73) Assignee: Coreana Cosmetics Co., Ltd. (KR)

( * ) Notice: Subject to any disclaimer, the term of this patent is extended or adjusted under 35 U.S.C. 154(b) by 0 days.

(21) Appl. No.: 09/715,626

(22) Filed: Nov. 17, 2000

(30) Foreign Application Priority Data

Dec. 23, 1999 (KR) ......................................... 1999-61030

(51) Int. Cl.⁷ ............................ A61K 7/00; A61K 38/00
(52) U.S. Cl. ............................ 424/401; 424/400; 514/2
(58) Field of Search ................................ 424/401; 514/2

(56) References Cited

U.S. PATENT DOCUMENTS

| | | | | |
|---|---|---|---|---|
| 4,603,146 A | | 7/1986 | Kligman | 514/559 |
| 4,877,805 A | | 10/1989 | Kligman | 514/381 |
| 5,492,894 A | * | 2/1996 | Bascom et al. | 514/18 |
| 6,020,139 A | * | 2/2000 | Schwartz et al. | 435/7.1 |

OTHER PUBLICATIONS

Sporn, M.B. amd Roberts, A.B., eds., *Handbook of Experimental Pharmacology: Peptide Growth Factors and Their ReceptorsI*, 4 Chapter 4, "The Epidermal Growth Factor Family," Springer–Verlag, Berlin (1990).

Carpenter, G., "Epidermal Growth Factor," *Ann. Rev. Biochem.*, 48:193–216 (1979).

* cited by examiner

*Primary Examiner*—Shelley A. Dodson
(74) *Attorney, Agent, or Firm*—Heslin Rothenberg Farley and Mesiti, P.C.; Candice J. Clement, Esq.

(57) ABSTRACT

A cosmetic composition for skin care containing retinol and epidermal growth factor is disclosed. In embodiments of the cosmetic composition, the epidermal growth factor is preferably present in an amount of 0.00001 to 1% by weight, and more preferably 0.0001 to 0.1% by weight, based on the total weight of the composition. The EGF-containing cosmetic composition of the present invention enhances the skin care effect of retinol and also alleviates adverse effects of retinol, such as skin irritation.

12 Claims, No Drawings

COSMETIC COMPOSITION FOR SKIN CARE CONTAINING RETINOL AND EPIDERMAL GROWTH FACTOR

PRIOR FOREIGN APPLICATION

This applications claims priority from Korean Patent Application Number KR 1999-61030 filed Dec. 23, 1999, the entire contents of which is incorporated herein by reference.

FIELD OF THE INVENTION

The present invention relates to a cosmetic composition for skin care, which enhances the skin care effect of retinol and also alleviates the adverse effect thereof

BACKGROUND OF THE INVENTION

Skin, which is the biggest organ of the human body, is composed of epidermis, dermis and subcutaneous fat. It performs various functions such as protection, barrier, temperature controlling, excretion and respiration. With the passage of time, however, those functions rapidly decline and a variety of changes occur to the skin. Physiological changes of the skin with aging, for example, include the decrease in thickness of epidermis, dermis and subcutaneous tissue; the dryness of skin resulting from the moisture reduction according to the changes of lipid composition and content in lipid barrier; and the occurrence of age spots, freckles, pigmentation or various skin lesions. Especially, the active oxygen species and free radicals, which can be generated by excess UV rays, air pollution, or fatigue or stress in modern life, oxidize or denature the bio-materials such as proteins, nucleic acids and membrane lipids, leading to the aging of the skin. Accordingly, there have been many studies on the occurrence of the wrinkles, age spots or freckles, the loss of skin elasticity, the pigmentation, and the dryness of skin.

A variety of cosmetic compositions have been developed in order to solve the problems with aging of the skin and some visible results have been obtained in improving skin wrinkles. Various clinical studies have been reported on the effects of cosmetic compositions containing retinoids in improving wrinkles, freckles and deposited pigments, especially of the compositions containing retinol (vitamin A) in improving wrinkles, sagging and the reduction in elasticity of skin formed by sunlight. Japanese Patent Laid-open Publication No. Hei 5-246838 discloses a method for improving wrinkles of skin by the synthesis of collagen. It teaches that the activity of collagenase that decomposes collagen to promote collagen metabolism might be reduced with aging, leading to the increase of cross-link collagens and the increase of skin wrinkles. U.S. Pat. Nos. 4,603,146 and 4,877,805 also disclose methods for improving skin wrinkles by using retinol that is effective in the synthesis of collagen and the inhibition from the decomposition thereof.

Retinol, an endogenous compound naturally present in the human body, is a lipo-soluble vitamin indispensable to the differentiation and growth of epithelial tissues. It is also believed to have an effect on the stimulation of physical growth and on the treatment of night blindness. In addition, when used in a cosmetic composition, retinol is believed to have an effect in enhancing the metabolism of skin cells, the differentiation and the resistance of the skin, and in inhibiting sebum secretion. Accordingly, there has been much interest in cosmetic compositions for skin care containing retinol. For example, various acne ointments containing retinol have been commercially available. Moreover, much effort has been invested in developing other uses of retinol, resulting in the application of retinol in treatment of UV damaged skin.

However, since retinol is extremely labile and thus easily oxidized and degenerated when exposed to air, vitamin A palmitate, a derivative of retinol, has been mainly used instead of retinol. But the recent tendency is back to the use of retinol itself because of the low stability and effect of vitamin A palmitate when applied to the skin. However, since the activity of retinol is rapidly decreased during storage, much research is still required in order to increase the shelf life of products containing retinol. At present, there has been research on encapsulating retinol with collagen, preventing retinol from air and light, or developing appropriate antioxidants.

Moreover, since retinol may cause skin irritation even with small doses, the use of retinol as an ingredient in cosmetics has been severely limited.

In the meantime, the Epidermal Growth Factor (EGF) is a strong promoter on the division of various epithelial cells originated in the ectoderm and mesoderm. It is extensively distributed in body fluid, especially in urine and breast milk (Carpenter, G. and Cohen, S., "Epidermal growth factor," Ann. Rev. Biochem., 48, 192–216 (1979)). It is a single polypeptide consisting of 53 amino acid residues and has a molecular weight of 6,200 Daltons (Campion, S. R. and Niyogi, S. K., "Interaction of epidermal growth factor with its receptor"). In 1962, Cohen isolated EGF from the gland beneath the chin of the mature male mouse. In 1972, Savage and Taylor identified the primary structure of mouse EGF and the location of three intramolecular disulfide bonds in EGF that are essential for physiological function. Gregory demonstrated in 1975 that the human EGF (hEGF) is identical with Urogastron, an inhibitory hormone of gastric acid secretion extracted from the urine of pregnant women.

EGF is believed to have an excellent effect on skin injuries because it strongly promotes the proliferation of epithelial cells, endothelial cells and fibroblasts, and also the migration and proliferation of epithelial cells to where they are deficient.

SUMMARY OF THE INVENTION

It is an object of the present invention to provide a cosmetic composition for skin care, which enhances the effect of retinol, one of the conventional skin-care ingredients, and also alleviates the adverse effects of retinol. More specifically, it is an object of the present invention to provide a skin-care cosmetic composition, which enhances the effect of retinol such as the treatment of acne, the improvement of skin wrinkles, age spots, freckles, blotches or other pigmentation, and the moisturizing of skin, and also alleviates adverse effects of retinol such as skin irritation.

The present inventors have found that EGF remarkably enhances the effect of retinol used in topical therapeutics and cosmetics, and also effectively alleviates the skin irritation of retinol.

DETAILED DESCRIPTION OF THE INVENTION

The present invention relates to a cosmetic composition for skin care containing retinol and EGF.

As used herein, 'improving skin wrinkles' means preventing, retarding, arresting, or even reversing skin wrinkles.

In the present invention, any human or nonhuman EGF, either natural or isolated from transformed microorganisms, can be used. Preferably, EGF isolated and purified from a recombinant E. coli (JM101) is used. In this case, EGF may be obtained by fermenting the recombinant E. coli for 48 to 72 hours according to the fed-batch method, and then isolating the fermented supernatant by Amberchrome CG71 chromatography and Q-sepharose chromatography (see U.S. Pat. No. 5,652,120; Japanese Patent No. 2,609,515; European Patent No. 652954; and Korean Patent Nos. 102993, 107023, 110123 and 114856). Furthermore, the above patents confirm that EGF isolated and purified from the recombinant E. coli is identical to the human EGF.

In the cosmetic composition of the present invention, EGF is preferably used in an amount of 0.00001 to 1% by weight, and more preferably, 0.0001 to 0.1% by weight based on the total weight of the cosmetic composition.

The amount of retinol used in the cosmetic composition of the present invention is preferably from 0.001 to 5.0% by weight, and more preferably 0.01 to 2.0% by weight based on the total weight of the cosmetic composition.

Examples of formulations of the cosmetic composition of the present invention include, but are not limited to, skin softener, astringent, nutrient emulsion, eye cream, nutrient cream, massage cream, cleansing cream, cleansing foam, cleansing water, powder, essence and facial pack.

In addition to retinol and EGF, other suitable ingredients can be added to the cosmetic composition of the present invention depending on the type of the cosmetic formulation or the purpose of the use.

The following examples are to exemplify the various aspects of carrying out the present invention and are not intended to limit the invention in any way.

EXAMPLE 1 AND COMPARATIVE EXAMPLE 1

The cosmetic compositions of Example 1 and Comparative example 1 were prepared using the components listed in Table 1 below.

TABLE 1

| Ingredients | Example 1 (% by weight) | Comparative Example 1 (% by weight) |
|---|---|---|
| EGF | 0.001 | — |
| Retinol | 2.0 | 2.0 |
| Vaseline | 7.0 | 7.0 |
| Liquid paraffin | 10.0 | 10.0 |
| Wax | 2.0 | 2.0 |
| Polysorbate 60 | 2.0 | 2.0 |
| Sorbitan sesquioleate | 2.5 | 2.5 |
| Squalene | 3.0 | 3.0 |
| Propylene glycol | 6.0 | 6.0 |
| Glycerin | 4.0 | 4.0 |
| Triethanolamine | 0.5 | 0.5 |
| Carboxyvinylpolymer | 0.1 | 0.5 |
| Tocopherylacetate | 0.1 | 0.1 |
| Flavor | 0.2 | 0.2 |
| Methylparaben | 0.2 | 0.2 |
| Imidazolidinyl Urea | 0.2 | 0.2 |
| Purified water | q.s. | q.s. |

Experimental Example 1

Skin Wrinkle Improvement Effect

The effects of the cosmetic compositions of Example 1 and Comparative Example 1 on skin wrinkle improvement were determined as follows.

It involved twenty female subjects of 30 years and over, who were divided into two groups (A and B). The cosmetic compositions of Example 1 and Comparative Example 1 were applied on the upper arms (area of 2×2 cm$^2$) of the groups A and B, respectively, twice a day with dose of 0.2 g for 12 weeks. Then, replicas of their skin wrinkles were prepared using transparent silicon solution. The changes in the skin wrinkles of the replicas were detected with Skin Visiometer (SV400 manufactured by C+K Electronics GmbH, Germany). Then three-dimensional images of the replicas were analyzed with a CCD camera. The skin wrinkle improvement effect was determined as average roughness of the wrinkles ($R_z$) according to the following numerical formula I:

$$R_z = \frac{R_1 + R_2 + R_3 + \cdots R_{m-2} + R_{m-1} + R_m}{\text{Number of wrinkles}(m)} \quad (I)$$

Wherein, $R_m$ is the roughness of each wrinkle and m is the number of the wrinkles. The results are shown in Table 2 below.

TABLE 2

Skin wrinkle improvement effect (12 weeks)

average roughness of the wrinkles ($R_z$, μm)

| | Example 1 | | | Comparative Example 1 | | |
|---|---|---|---|---|---|---|
| | T0 | T12 | ΔR$_z$ | T0 | T12 | ΔR$_z$ |
| Subject 1 | 120 | 63 | −57 | 128 | 101 | −27 |
| Subject 2 | 115 | 32 | −83 | 141 | 91 | −50 |
| Subject 3 | 125 | 22 | −103 | 133 | 97 | −36 |
| Subject 4 | 140 | 56 | −84 | 107 | 72 | −35 |
| Subject 5 | 129 | 57 | −72 | 93 | 70 | −23 |
| Subject 6 | 112 | 33 | −79 | 119 | 93 | −26 |
| Subject 7 | 123 | 45 | −78 | 122 | 75 | −47 |
| Subject 8 | 132 | 32 | −100 | 135 | 107 | −28 |
| Subject 9 | 105 | 21 | −84 | 148 | 102 | −46 |
| Subject 10 | 137 | 39 | −98 | 127 | 99 | −28 |
| Average | | | −83.8 | | | −34.6 |

T0: the initial $R_z$
T12: the $R_z$ determined at week 12
ΔR$_z$: the value of T0 minus T12

As can be seen from the above, the height (roughness) of the wrinkles was decreased by 83.8 μm (p<0.01) after 12 weeks use of the cosmetic composition in Example 1, which means 242.2% improvement over that in Comparative Example 1. This result shows that EGF greatly enhances the effect of retinol on wrinkle improvement. It also shows that the cosmetic composition of the present invention exhibits a visible effect on wrinkle improvement in a very short time, while it takes a long time for conventional wrinkle treatment cosmetics to exhibit it.

Experimental Example 2

Skin Wrinkle Improvement Effect

The effects of the cosmetic compositions in Example 1 and Comparative Example 1 were determined as follows.

Twenty female subjects of 30 years and over (average age of 37.7 years) were divided into two groups (A and B). Then the cosmetic compositions of Example 1 and Comparative Example 1 were applied around the eyes of the subjects in groups A and B, respectively, for 12 weeks. A panel of specialists evaluated the improvement of the subjects' eye wrinkles according to the following scale graded from −3 to 3. The subjects themselves also evaluated the improvement of the wrinkles in the same manner. Those results are shown in Table 3 and 4, respectively.

Grade Scale for the Improvement of the Skin Wrinkles

−3: very worsened
−2: worsened
−1: a little worsened
0: not changed
1: a little improved
2: moderately improved
3: remarkably improved

TABLE 3

Wrinkle improvement effect
(The objective evaluation of the specialists)

| | Grade of skin wrinkle improvement | | | |
|---|---|---|---|---|
| | Example 1 | | Comparative Example 1 | |
| | T0 | T12 | T0 | T12 |
| Subject 1 | 0 | 3 | 0 | 3 |
| Subject 2 | 0 | 3 | 0 | 2 |
| Subject 3 | 0 | 3 | 0 | 2 |
| Subject 4 | 0 | 2 | 0 | 1 |
| Subject 5 | 0 | 2 | 0 | 2 |
| Subject 6 | 0 | 3 | 0 | 1 |
| Subject 7 | 0 | 2 | 0 | 2 |
| Subject 8 | 0 | 3 | 0 | 2 |
| Subject 9 | 0 | 2 | 0 | 1 |
| Subject 10 | 0 | 2 | 0 | 2 |
| ΔW | | 2.5 | | 1.8 |

T0: the initial grade
T12: the grade determined at week 12
ΔW: the average grade of T12 minus T0.

TABLE 4

Wrinkle improvement effect
(The subjective evaluation of the subjects)

| | Grade of skin wrinkles | | | |
|---|---|---|---|---|
| | Example 1 | | Comparative Example 1 | |
| | T0 | T12 | T0 | T12 |
| Subject 1 | 0 | 2 | 0 | 1 |
| Subject 2 | 0 | 3 | 0 | 3 |
| Subject 3 | 0 | 3 | 0 | 1 |
| Subject 4 | 0 | 3 | 0 | 1 |
| Subject 5 | 0 | 3 | 0 | 2 |
| Subject 6 | 0 | 2 | 0 | 1 |
| Subject 7 | 0 | 1 | 0 | 2 |
| Subject 8 | 0 | 3 | 0 | 3 |
| Subject 9 | 0 | 3 | 0 | 1 |
| Subject 10 | 0 | 1 | 0 | 1 |
| ΔW | | 2.4 | | 1.6 |

T0: the initial grade
T12: the grade determined at week 12
ΔW: the average grade of T12 minus T0.

As can be seen from the above, the objective and subjective evaluations in case of Example 1 were 2.5 and 2.4, respectively, which is 38.9% and 50% improvement over those of Comparative Example 1. These results demonstrate that EGF enhances the effect of retinol on skin wrinkle improvement.

Experimental Example 3

Skin Elasticity Improvement Effect

The effects of the cosmetic compositions of Example 1 and Comparative Example 1 on skin elasticity were determined in the following manner.

It involved fifteen healthy female subjects (average age of 36.3 years). The cosmetic composition of Example 1 was applied around the left eye of the subjects and the cosmetic composition prepared by Comparative Example 1 was applied around the right eye of the subjects, at the temperature of 24 to 26° C. and 75% RH for 12 weeks. The skin elasticity improvement was evaluated using Cutometer (SEM 575, C+K Electronic Co., Germany). The results are shown in Table 5 below as (Δ R8) representing the change of viscoelasticity of the skin.

TABLE 5

Skin elasticity improvement Effect

| | Skin elasticity improvement (ΔR8) |
|---|---|
| Example 1 | 0.35 |
| Comparative Example 1 | 0.09 |

As can be seen in Table 5, when using the EGF-containing cosmetic composition of Example 1, skin elasticity was increased by 289% over that of Comparative Example 1. This result demonstrates that EGF enhances the effect of retinol on promoting the synthesis of collagen and increase skin elasticity. It appears that EGF effectively promotes the physiological activity of the cells and thus the increase of skin elasticity by retinol can be rapidly obtained.

Experimental Example 4

Skin Moisturizing Effect

The skin moisturizing effects of the cosmetic compositions of Example 1 and Comparative Example 1 were determined in the following manner.

The cosmetic composition of Example 1 was applied on the upper arms of fifteen healthy female subjects (average age of 36.3 years) three times a day for 6 weeks, at the temperature of 25° C. and 45% RH in a room with no flow of air. The trans-epidermal water loss (TEWL) of the applicated-area was measured using TEWAMETER TM210 (C+K electronic GmbH, Germany) and the changes (Δ TEWL) of TEWL with the passage of time were calculated. In addition, the skin moisturizing effect was determined as the change of the conductivity according to the change of water content in epidermis using CORNEOMETER CM 820 PC (C+K electronic GmbH, Germany). The water content of epidermis was represented by a value within a range of 0 to 150. The results are shown in Table 6 below.

TABLE 6

Skin moisturizing effect

| | ΔTEWL (g/hm$^2$) | Corneometer Value |
|---|---|---|
| Example 1 | 4.5 | 124 |
| Comparative Example 1 | 2.7 | 108 |

As can be seen in Table 6, A TEWL value of the cosmetic composition of Example 1 is 4.5 g/hm$^2$, which means that the transepidermal water loss is greatly improved over that of the composition of Comparative Example 1. Moreover, the cosmetic composition of Example 1 showed higher corneometer value than that of Comparative Example 1.

Experimental Example 5

Skin Safety Test

The cosmetic compositions of Example 1 and Comparative Example 1 were tested for their safety to skin as follows.

Thirty subjects (19–34 years; average age of 22 years) were divided into two groups (A and B). The patch test using Haye's Test Chamber was carried out to both groups, in which the cosmetic composition of Example 1 was applied to the skin of the subject group A, and the cosmetic composition of Comparative Example 1 was applied to the skin of the subject group B. In the test, people suffering from psoriasis, eczema and other skin diseases, pregnant women, breast-feeding women, or the ones taking medicines such as contraceptives and antihistamines were excluded.

First, the forearms of the subject group A and B were cleaned with 70% ethanol and dried. Then, each 15 μg of the cosmetic compositions of Example 1 and Comparative Example 1 were dropped into the Test Chambers separately and then the Chambers were patched on the cleaned upper arms of the subject group A and B separately. After 24 hours, the patches were removed and then the test areas were marked with a marking pen. After each lapse of 24, 48 and 72 hours, the test areas were observed.

The skin response was checked 24, 48 and 72 hours after the removal of the patch, according to the criteria of International Contact Dermatitis Research Group (ICDRG) as shown in Table 7 below.

TABLE 7

| Symbol | Judge criteria for the skin response | Evaluation | Average |
|---|---|---|---|
| ± | Doubtful or slight reaction and erythema | Minute irritation | 0 to 0.9 |
| + | Erythema + Induration | Mild irritation | 1.0 to 2.9 |
| ++ | Erythema + Induration + Vesicle | Moderate irritation | 3.0 to 4.9 |
| +++ | Erythema + Induration + Bullae | Severe irritation | 5.0 or more |
| − | Negative | No irritation | 0 |

The results are shown in Table 8 below.

TABLE 8

| Elapsed Time | Example 1 | Comparative Example 1 |
|---|---|---|
| 24 hours | 0 | 2.0 |
| 48 hours | 0 | 0.5 |
| 72 hours | 0 | 0.1 |

As can be seen in Table 8, the cosmetic composition of Example 1 caused no irritation to the skin, which proved to be safe. In contrast, the cosmetic composition of Comparative Example 1 caused some irritation to the skin, which shows that retinol is irritating to skin. Therefore, it was confirmed that EGF enhances the effect of retinol and also effectively alleviates the irritation caused by retinol.

Experimental 6

Stinging Potential Test

The cosmetic compositions of Example 1 and Comparative Example 1 were tested for their stinging potential to the skin as follows.

Twenty subjects of 19 to 34 years (average age of 22 years) were sufficiently sweated out using a steam generator for 15 minutes, and then the left cheek of each subject was intensely rubbed with the cosmetic composition of Example 1 and the right cheek of each subject was intensely rubbed with the cosmetic composition of Comparative Example 1. The response of the facial skin (such as itching, tingle, sore, rash and swelling) was observed for 8 minutes. In the test, people suffering from psoriasis, eczema and other skin diseases, pregnant women, breast-feeding women, or the ones taking medicines such as contraceptives and antihistamines were excluded in this test.

The stinging grade was classified into intense stinging, mild stinging, moderate stinging and delayed stinging where the irritation response appeared within 30 seconds, 2.5 minutes, 5 minutes and 8 minutes, respectively, after the application of the cosmetic composition. In addition, the response rate (%) was calculated by dividing the response score by the number of subjects. The stinging grade was evaluated on the basis of the response rate according to the criteria represented in Table 9.

TABLE 9

| Grade | Response Rate (%) | Evaluation |
|---|---|---|
| 1 | 0.00 to 0.75 | No Stinging |
| 2 | 0.76 to 1.50 | Delayed Stinging |
| 3 | 1.51 to 2.50 | Mild Stinging |
| 4 | 2.51 to 4.00 | Moderate Stinging |
| 5 | 4.01 or more | Intense Stinging |

The results of the skin-stinging test for the cosmetic compositions of Example 1 and Comparative Example 1 are shown in Table 10 below.

TABLE 10

| | Example 1 | Comparative Example 1 |
|---|---|---|
| Response Rate (%) | 0.7 | 1.28 |
| Evaluation | No Stinging | Delayed Stinging |
| Grade | 1 | 2 |

As can be seen from the above results, the cosmetic composition of Example 1 yielded the response rate of 0.7% and was evaluated as no stinging. In contrast, the cosmetic composition of Comparative Example 1 containing only retinol yielded the response rate of 1.28% and was evaluated as delayed stinging. The irritation degree yielded by the cosmetic composition of Comparative Example 1 is almost equal to that yielded by a cream containing retinol. This confirms that retinol is stinging to skin. Therefore, it is recognized that EGF prevents the irritation of retinol to the skin.

Experimental Example 7

Formulation Stability Test

Stability was tested for the formulations of the cosmetic compositions prepared by Example 1 and Comparative Example 1 as follows.

The cosmetic compositions of Example 1 and Comparative Example 1 were put in opaque glass vessels separately which were then kept in a thermostatic chamber at 45° C. for 12 weeks. In addition, the cosmetic compositions of Example 1 and Comparative Example 1 were put in other opaque glass vessels and were stored in a light-shield refrigerator at the constant temperature of 4° C. for 12 weeks. The phase separation of the cosmetic composition and the change of the cosmetic composition in color were evaluated at week 12 on a scale graded from 0 to 6 as follows:

Grade Scale for the Phase Separation and the Change in Color

- 0: No phase separation (discoloration)
- 1: Minute phase separation (discoloration)
- 2: Mild phase separation (discoloration)
- 3: Moderate phase separation (discoloration)
- 4: Severe phase separation (discoloration)
- 5: Very severe phase separation (discoloration)

The results are shown in Table 11 below.

TABLE 11

| Temperature | Grade of discoloration | |
|---|---|---|
| | Example 1 | Comparative Example 1 |
| 45° C. | 0 | 1.5 |
| 4° C. | 0 | 0 |

As can be seen in the above Table 11, the cosmetic composition of Example 1 did not show any separation or change in color, which proved to be stable. In contrast, the cosmetic composition of Comparative Example 1 containing only retinol was changed in color at 45° C. It shows that retinol is labile to the temperature.

From the viewpoint of the above results, it is appreciated that the cosmetic composition of the present invention not only prevents the problems caused by retinol such as the skin irritation and the instability of the formulation but also remarkably improves the beneficial effect of retinol.

The following examples illustrate the formulations of the cosmetic composition according to the present invention but are not intended to limit the invention in any way.

Formulation Example 1: Skin softener (Skin lotion)

| Ingredients | Amounts (% by weight) |
|---|---|
| Retinol | 0.01 |
| EGF | 0.0001 |
| 1,3-Butyleneglycol | 6.0 |
| Glycerin | 4.0 |
| Oleyl alcohol | 0.1 |
| Polysorbate 20 | 0.5 |
| Ethanol | 15.0 |
| Benzophenone-9 | 0.05 |
| Flavor | 0.2 |
| Methylparaben | 0.2 |
| Imidazolidinyl Urea | 0.2 |
| Purified water | q.s. |

Formulation Example 2: Nutrient emulsion (Milk lotion)

| Ingredients | Amounts (% by weight) |
|---|---|
| Retinol | 0.5 |
| EGF | 0.0002 |
| Propyleneglycol | 6.0 |
| Glycerin | 4.0 |
| Triethanolamine | 1.2 |
| Tocopherylacetate | 3.0 |
| Liquid paraffin | 5.0 |
| Squalene | 3.0 |
| Makadamia nut oil | 2.0 |
| Polysorbate 60 | 1.5 |
| Sorbitan sesquioleate | 1.0 |
| Carboxyvinylpolymer | 1.0 |
| Flavor | 0.2 |
| Methylparaben | 0.2 |
| Imidazolidinyl Urea | 0.2 |
| Purified water | q.s. |

Formulation Example 3: Nutrient cream

| Ingredients | Amounts (% by weight) |
|---|---|
| Retinol | 1.0 |
| EGF | 0.0005 |
| Vaseline | 7.0 |
| Liquid paraffin | 10.0 |
| Wax | 2.0 |
| Polysorbate 60 | 2.0 |
| Sorbitan sesquioleate | 2.5 |
| Squalene | 3.0 |
| Propyleneglycol | 6.0 |
| Glycerin | 4.0 |
| Triethanolamine | 0.5 |
| Carboxyvinylpolymer | 0.5 |
| Tocopherylacetate | 0.1 |
| Flavor | 0.2 |
| Methylparaben | 0.2 |
| Imidazolidinyl Urea | 0.2 |
| Purified water | q.s. |

Formulation Example 4: Massage cream

| Ingredients | Amounts (% by weight) |
|---|---|
| Retinol | 0.5 |
| EGF | 0.0002 |
| Propyleneglycol | 6.0 |
| Glycerin | 4.0 |
| Triethanolamine | 0.5 |
| Wax | 2.0 |
| Tocopherylacetate | 0.1 |
| Polysorbate 60 | 3.0 |
| Sorbitan sesquioleate | 2.5 |
| Cetearyl alcohol | 2.0 |
| Liquid paraffin | 30.0 |
| Carboxyvinylpolymer | 0.5 |
| Flavor | 0.2 |
| Methylparaben | 0.2 |
| Imidazolidinyl Urea | 0.2 |
| Purified water | q.s. |

Formulation Example 5: Facial pack

| Ingredients | Amounts (% by weight) |
|---|---|
| Retinol | 1.0 |
| EGF | 0.0005 |

-continued

Formulation Example 5: Facial pack

| Ingredients | Amounts (% by weight) |
|---|---|
| Propyleneglycol | 2.0 |
| Glycerin | 4.0 |
| Carboxyvinylpolymer | 0.3 |
| Ethanol | 7.0 |
| PEG-40 Hydrogenated Castor Oil | 0.8 |
| Triethanolamine | 0.3 |
| Flavor | 0.2 |
| Methylparaben | 0.2 |
| Imidazolidinyl Urea | 0.2 |
| Purified water | q.s. |

What is claimed is:

1. A cosmetic composition for skin care, consisting essentially of retinol and epidermal growth factor.

2. The cosmetic composition according to claim 1, wherein the epidermal growth factor is isolated and purified from a recombinant *E. coli*.

3. The cosmetic composition according to claim 1, wherein the epidermal growth factor is present in an amount of 0.00001 to 1% by weight based on the total weight of the composition.

4. The cosmetic composition according to claim 3, wherein the epidermal growth factor is present in an amount of 0.0001 to 0.1% by weight based on the total weight of said composition.

5. The cosmetic composition according to claim 1, wherein the retinol is present in an amount of 0.001 to 5.0% by weight based on the total weight of said composition.

6. The cosmetic composition according to claim 5, wherein the retinol is present in an amount of 0.01 to 2.0% by weight based on the total weight of said composition.

7. The cosmetic composition according to claim 1, wherein the composition is in the form of a skin softener, a nutrient emulsion, a nutrient cream, a massage cream or a facial pack.

8. The cosmetic composition according to claim 2, wherein the epidermal growth factor is present in an amount of 0.00001 to 1% by weight based on the total weight of the composition.

9. The cosmetic composition according to claim 8, wherein the epidermal growth factor is present in an amount of 0.0001 to 0.1% by weight based on the total weight of the composition.

10. The cosmetic composition according to claim 2, wherein the retinol is present in an amount of 0.001 to 5.0% by weight based on the total weight of the composition.

11. The cosmetic composition according to claim 10, wherein the retinol is present in an amount of 0.01 to 2.0% by weight based on the total weight of the composition.

12. The cosmetic composition according to claim 2, wherein the composition is in the form of a skin softener, a nutrient emulsion, a nutrient cream, a massage cream or a facial pack.

* * * * *